United States Patent [19]

Hoyle et al.

[11] 4,393,006

[45] Jul. 12, 1983

[54] DIAZIDOSULFONYL-N-SUBSTITUTED ANILINE

[75] Inventors: Charles E. Hoyle; Ronald S. Lenox, both of Lancaster, Pa.

[73] Assignee: Armstrong World Industries, Inc., Lancaster, Pa.

[21] Appl. No.: 396,016

[22] Filed: Jul. 7, 1982

[51] Int. Cl.³ .................................. C07C 161/00
[52] U.S. Cl. .................................. 260/349; 544/277; 546/312; 548/193; 548/557; 548/558; 549/480
[58] Field of Search .............. 260/349; 548/193, 557, 548/558; 549/480; 546/312; 544/277

[56] References Cited

PUBLICATIONS

Gevaert-Agfa, *Chemical Abstracts,* vol. 64 (1966), No. 15232f.

*Primary Examiner*—Robert W. Ramsuer

[57] ABSTRACT

Novel diazidosulfonyl-N-substituted aniline compounds are disclosed. These compounds are useful in pretreating cellulosic materials to thereby photolytically develop colored images on said materials.

8 Claims, No Drawings

DIAZIDOSULFONYL-N-SUBSTITUTED ANILINE

DESCRIPTION OF THE INVENTION

The novel compounds of the present invention correspond to formula 1:

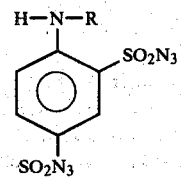

wherein R is $C_1$–$C_{15}$ alkyl, $C_2$–$C_{15}$ unsaturated alkyl, aryl, $C_3$–$C_{15}$ cycloalkyl or a heterocyclic radical.

The term "$C_1$–$C_{15}$ alkyl" is used in the specification and claims to signify a straight or branched alkyl group containing from 1 to 15 carbon atoms.

The term "heterocyclic radical" is used in the present specification and claims in its art recognized sense to indicate a ringed moiety which contains in its ring atoms, in addition to carbon, at least one of nitrogen, oxygen and/or sulfur. The heterocyclic radicals utilized in the present invention will contain from about 5 to about 15 ring atoms and can contain from 1 to 3 ring groups. Examples of suitable heterocyclic radicals include but are not limited to pyrrole, furan, pyridine, purine and thiazole. The radicals may be unsubstituted or substituted in up to two positions with a substituent selected independently from alkyl groups, halogen, oxygen or nitrogen moieties.

The term "aryl" is used in the specification and claims to signify phenyl or naphthyl, both of which may be unsubstituted or substituted in up to two positions with a substituent selected independently from $C_1$–$C_4$ alkyl, halo or —$NO_2$. "$C_1$–$C_4$ alkyl" is used above to signify a straight or branched alkyl group containing from 1 to 4 carbon atoms and "halo" is used above to signify fluoro, chloro, iodo and bromo.

The term "$C_3$–$C_{15}$ cycloalkyl" is used in its art recognized sense to indicate a cyclic alkane radical having from 3 to 15 carbon atoms.

The term "$C_2$–$C_{15}$ unsaturated alkyl" is used in the specification and claims to signify a straight or branched alkyl group containing at least 1 carbon-carbon double bond and having from 2 to 15 carbon atoms.

The novel compounds of the present invention are prepared by first subjecting the corresponding N-substituted acetanilide to chlorosulfonation to form a chlorosulfonyl intermediate. This intermediate is then reacted with sodium azide to thereby prepare the desired diazidosulfonyl-N-substituted aniline. The reaction is exemplified by the following equation:

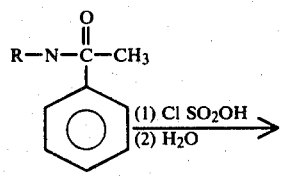

-continued

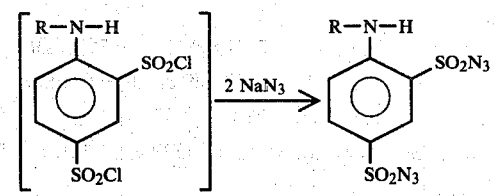

wherein R is as defined above.

The chlorosulfonation reaction is maintained at from about 100° C. to about 140° C. until completed, usually from about 10 to about 60 minutes or until gas evolution ceases. The chlorosulfonyl intermediate is dissolved in a suitable solvent, such as acetone or methyl ethyl ketone. An aqueous solution of sodium azide is then added to the resulting solution and the resulting reaction mixture is maintained at from about 0° C. to about 50° C. with agitation until substantial completion of the reaction, usually from about 15 to about 120 minutes. Upon completion of the reaction, the reaction mixture is added to a large excess of water. The crude product precipitates, is recovered by filtration and is purified, such as by being recrystallized from toulene, and dried.

The N-substituted acetanilide starting materials are available commercially or can be produced by the known reactions of the corresponding amine with acid anhydrides or acid chlorides set forth in *Vogel's Elementary Practical Organic Chemistry; Preparations*, 3rd Edition, Longman Group Ltd., London, 1980. N-Methylacetanilide, which is utilized in Example 1 below was synthesized from N-methylaniline by reaction with acetic anhydride.

The compounds of the present invention are used to pretreat cellulosic materials such as wood or paper to make such materials susceptible to being colored photolytically. For such pretreatment operations, a solution is first formed of at least one compound of the present invention. Optionally, a nitrogen-containing compound or polymer may also be dissolved in the solvent. The cellulosic material is then contacted with the solution in the pretreatment operation. The thus treated material can then be exposed to a UV-emitting light source to thereby photolytically develop a color on the material. The use of nitrogen-containing polymers helps to increase the washfastness of the resultant color on the cellulosic material.

EXAMPLE 1

This example illustrates the preparation of 2,4-diazidosulfonyl-N-methylaniline.

N-Methylacetanilide (41.0 g, 0.275 mol) was dissolved in 300 g cholorosulfonic acid and slowly heated to 120° C. Only at this temperature did gas evolution become obvious indicating that chlorosulfonation was occurring. When gas evolution had ceased, the reaction was heated for an additional thirty minutes and poured onto ice to give a white sticky material.

The white material was dissolved in 900 ml of acetone. Sodium azide (17.9 g, 0.275 mol) was dissolved in 75 ml $H_2O$ and added at once. After one hour of vigorous stirring, the reaction mixture was poured into 3 liters of water. This was stirred for 15 minutes; the white solid which precipitated was collected by suction filtration to give 11.2 g of the product compound (FIG. 2) as a white solid; (0.044 mol, 16.0% based on N-methylacetanilide). This material was recrystallized from toluene; mp 118°–120° C. with detonation of the melt.

NMR (CDCl$_3$): 3.03(d,3H), 6.55(s,1H—N$\underline{\text{H}}$), 6.90(d,J=8 Hz,1H), 7.96(d of d, J$_A$=8 Hz, J$_B$=2 Hz,1H), 8.32(d,J=2 Hz,1H).

IR (KBr): 3400(m), 2139(s), 1600(s), 1355(m), 1162(s), 750 cm$^{-1}$(s).

Calcd. for C$_7$H$_7$N$_7$O$_4$S: C,26.49; H,2.22; N,30.90; S,20.20. Found: C,27.15; H,2,21; N,29.43; S,20.36.

The detonation of the melt noted above is indicative of the instability of this compound. The analysis values indicate that nitrogen may have been lost during analysis or shipment to the analyst. Therefore, Example 2 was run to confirm the structure of the desired product compound.

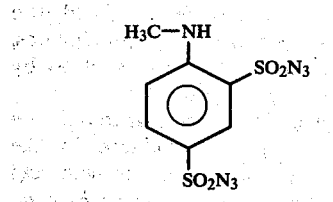

Formula 2:

EXAMPLE 2

In this example, the structure of the compound produced in Example 1 was further substantiated. The compound produced in Example 1 (2.0 g, 0.00786 mol) was decomposed in refluxing xylene to give an orange solid. Thermolysis should result in the formation of intermediate sulfonyl nitrenes with insertion into the C—H bonds of xylene and the N—H bond of the amino group with the compound of FIG. 3 as the product. The orange solid was recrystallized from toluene after decolorization with charcoal to give 0.53 g (0.0015 mol, 20.3% yield of the compound of FIG. 3 as a white solid; mp 215°–218° C.

NMR (DMSO-d$_6$): 1.94(s,3H), 2.18(s,3H, 3.23(s,3H), 6.80–7.40(mult.6H), 7.08(s,1H), 9.40(s,1H).

IR (KBr): 3400(m), 3256(s), 3176(m), 1610(w), 1499(s), 1372(m), 1303(s), 1150(s), 693 cm$^{-1}$(m).

Calcd. for C$_{15}$H$_{17}$N$_3$O$_4$S$_2$: C,49.03; H,4.66; N,11.44. Found: C,49.03; H,4.66; N,11.47.

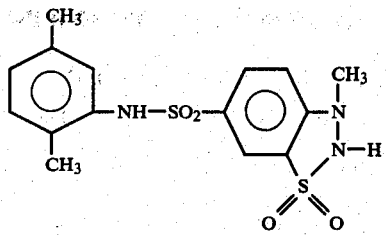

Formula 3:

Following the procedure of Example 1, and using N-Ethyl acetanilide, N-Propyl acetanilide, N-Butyl acetanilide (all of which are available from Pfaltz and Bauer, Inc.), the following compounds can, respectively, be produced:
2,4-Diazidosulfonyl-N-ethylaniline;
2,4-Diazidosulfonyl-N-propylaniline; and
2,4-Diazidosulfonyl-N-butylaniline.

Acetylation of N-isobutylaniline (ICN—K&K Laboratories, Inc.), N-cyclohexylaniline or N-allylaniline (both Pfaltz and Bauer, Inc.) followed by application of the procedure in Example 1 can result, respectively, in the following compounds:
2,4-Diazidosulfonyl-N-isobutylaniline;
2,4-Diazidosulfonyl-N-cyclohexylaniline; and
2,4-Diazidosulfonyl-N-allylaniline.

What is claimed is:

1. A compound having the formula

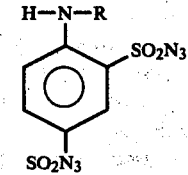

wherein R represents C$_1$–C$_{15}$ alkyl, C$_2$–C$_{15}$ unsaturated alkyl, C$_3$–C$_{15}$ cycloalkyl, aryl or a heterocyclic radical.

2. The compound of claim 1 which is 2,4-Diazidosulfonyl-N-methylaniline.

3. The compound of claim 1 which is 2,4-Diazidosulfonyl-N-ethylaniline.

4. The compound of claim 1 which is 2,4-Diazidosulfonyl-N-butylaniline.

5. The compound of claim 1 which is 2,4-Diazidosulfonyl-N-propylaniline.

6. The compound of claim 1 which is 2,4-Diazidosulfonyl-N-isobutylaniline.

7. The compound of claim 1 which is 2,4-Diazidosulfonyl-N-cyclohexylaniline.

8. The compound of claim 1 which is 2,4-Diazidosulfonyl-N-allylaniline.

* * * * *